United States Patent
Pratt et al.

(10) Patent No.: US 8,992,494 B2
(45) Date of Patent: Mar. 31, 2015

(54) SYSTEMS AND METHODS FOR DELIVERING FLUID TO A WOUND THERAPY DRESSING

(71) Applicants: Benjamin A. Pratt, Poole (GB); Kingsley Robert George Flower, Hampshire (GB); Richard Daniel John Coulthard, Verwood (GB); Mike Beasley, Wimborne (GB); Daniel Evans, Mumbles (GB)

(72) Inventors: Benjamin A. Pratt, Poole (GB); Kingsley Robert George Flower, Hampshire (GB); Richard Daniel John Coulthard, Verwood (GB); Mike Beasley, Wimborne (GB); Daniel Evans, Mumbles (GB)

(73) Assignee: KCI Licensing, Inc., San Antonio, TX (US)

( * ) Notice: Subject to any disclaimer, the term of this patent is extended or adjusted under 35 U.S.C. 154(b) by 14 days.

(21) Appl. No.: 13/752,180

(22) Filed: Jan. 28, 2013

(65) Prior Publication Data

US 2013/0204210 A1    Aug. 8, 2013

Related U.S. Application Data

(60) Provisional application No. 61/594,033, filed on Feb. 2, 2012.

(51) Int. Cl.
*A61M 1/00* (2006.01)
*A61M 35/00* (2006.01)
*A61M 3/02* (2006.01)

(52) U.S. Cl.
CPC ............. *A61M 1/0031* (2013.01); *A61M 35/00* (2013.01); *A61M 1/0058* (2013.01);
(Continued)

(58) Field of Classification Search
CPC . A61M 1/008; A61M 1/0088; A61M 1/0023; A61M 1/0037; A61M 1/0058; A61M 2205/3331; A61M 2205/3334; A61M 2205/3341; A61M 1/00; A61M 35/00; A61M 1/0031; A61F 2013/00536; A61F 2007/0059; A61F 2007/0069; A61F 2013/0017
USPC .................................................. 604/290, 319
See application file for complete search history.

(56) References Cited

U.S. PATENT DOCUMENTS 1,355,846 A    10/1920    Rannells
2,547,758 A    4/1951     Keeling
(Continued)

FOREIGN PATENT DOCUMENTS

AU    550575 A1    8/1982
AU    745271       4/1999
(Continued)

OTHER PUBLICATIONS

N.A. Bagautdinov, "Variant of External Vacuum Aspiration in the Treatment of Purulent Diseases of the Soft Tissues," Current Problems in Modem Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Leslie Deak
*Assistant Examiner* — Kai Weng

(57) ABSTRACT

Provided are systems and methods for delivery of fluid to a wound therapy dressing. In exemplary embodiments, a pressure source provides negative pressure to a wound dressing and a biasing mechanism provides positive pressure to a fluid reservoir.

20 Claims, 4 Drawing Sheets

(52) U.S. Cl.
CPC .......... *A61M 1/0084* (2013.01); *A61M 1/0088* (2013.01); *A61M 3/0233* (2013.01); *A61M 2205/15* (2013.01); *A61M 2205/3334* (2013.01); *A61M 2205/3344* (2013.01)
USPC .......................... 604/319; 604/290; 604/257

(56) References Cited

U.S. PATENT DOCUMENTS

| | | | |
|---|---|---|---|
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,367,332 A | | 2/1968 | Groves |
| 3,520,300 A | | 7/1970 | Flower Jr. |
| 3,568,675 A | | 3/1971 | Harvey |
| 3,648,692 A | | 3/1972 | Wheeler |
| 3,682,180 A | | 8/1972 | McFarlane |
| 3,826,254 A | | 7/1974 | Mellor |
| 3,989,169 A | * | 11/1976 | Bigley et al. .................. 222/207 |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,773,897 A | * | 9/1988 | Scheller et al. .................. 604/34 |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt et al. |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 6,071,267 A | | 6/2000 | Zamierowski |
| 6,135,116 A | | 10/2000 | Vogel et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |
| 6,814,079 B2 | | 11/2004 | Heaton et al. |
| 2002/0077661 A1 | | 6/2002 | Saadat |
| 2002/0115951 A1 | | 8/2002 | Norstrem et al. |
| 2002/0120185 A1 | | 8/2002 | Johnson |
| 2002/0143286 A1 | | 10/2002 | Tumey |
| 2002/0198503 A1 | | 12/2002 | Risk, Jr. et al. |
| 2010/0022990 A1 | | 1/2010 | Karpowicz et al. |
| 2010/0121287 A1 | * | 5/2010 | Smith et al. .................. 604/319 |
| 2011/0238110 A1 | * | 9/2011 | Wilke et al. .................. 606/216 |
| 2011/0306941 A1 | | 12/2011 | Chandrasekar et al. |

FOREIGN PATENT DOCUMENTS

| | | |
|---|---|---|
| AU | 455496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 333 965 A | 8/1999 |
| GB | 2 329 127 B | 8/2000 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |
| WO | WO 00/78372 A1 | 12/2000 |
| WO | WO 2008/098207 A2 | 8/2008 |

OTHER PUBLICATIONS

Louis C. Argenta, MD and Michael J. Morykwas, PhD; "Vacuum-Assisted Closure: A New Method for Wound Control and Treatment:

(56) References Cited

OTHER PUBLICATIONS

Clinical Experience"; Annals of Plastic Surgery, vol. 38, No. 6, Jun. 1997; pp. 563-576.
Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đ ukić, Ž. Maksimović, Đ . Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).
Partial International Search Report for corresponding PCT/US2013/023482.

\* cited by examiner

SYSTEMS AND METHODS FOR DELIVERING FLUID TO A WOUND THERAPY DRESSING

CROSS-REFERENCE TO RELATED APPLICATION

This application claims priority to U.S. Provisional Patent Application No. 61/594,033 filed Feb. 2, 2012, entitled SYSTEMS AND METHODS FOR DELIVERING FLUID TO A WOUND THERAPY DRESSING, the disclosure of which is hereby incorporated by reference in its entirety.

BACKGROUND

1. Field

The subject matter of this specification relates generally to healing of wounds and wound-treatment therapies. More particularly, but not by way of limitation, the subject matter relates to systems and methods for improving fluid-instillation and negative pressure wound therapy (NPWT) apparatuses and methods.

2. Discussion

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. The porous pad may be incorporated into a dressing having other components that facilitate treatment.

Typical instillation therapy instills fluid into a wound under a low positive pressure. For maximum therapeutic effect, the instilled fluid should reach all exposed tissue surfaces. The practice of fully filling a wound with instillation fluid, combined with the application of porous wound fillers and negative pressure to help distribute fluid, are techniques used to try and achieve good instillation therapy. Such techniques include numerous disadvantages, including difficulty in delivering the desired volume of fluid without overfilling the system and causing leakage.

Large volumes of fluid may be involved in certain systems, requiring frequent canister changes that may lead to user dissatisfaction. Although low positive pressures are typically used to fill the wound cavity, the hydraulic (essentially incompressible) nature of the fluid means that over filling can quickly cause leakage. Tortuous contours within a wound cavity may be difficult to reach with both foam dressings and liquid-fill techniques as gas pockets may be created. Applying a low vacuum during liquid instillation (to help maintain a seal and reduce leaking, to minimize patient discomfort, and to aid fluid distribution) can be problematic as instilled fluid may be removed before it is fully distributed through the dressing. Furthermore, the complexity of the system is increased when separate pumping mechanisms are incorporated into the wound therapy system.

The referenced shortcomings are not intended to be exhaustive, but rather are among many that tend to impair the effectiveness of previously known techniques in fluid delivery to wound dressings; however, those mentioned here are sufficient to demonstrate that the methodologies appearing in the art have not been satisfactory and that a significant need exists for the techniques described and claimed in this disclosure. For at least the reasons described above, improved wound treatment systems and methods are therefore desired.

SUMMARY

From the foregoing discussion, it should be apparent that a need exists for a system and method for improved delivery of fluid to a wound therapy dressing. The method in the disclosed embodiments substantially includes the steps necessary to carry out the functions presented above with respect to the operation of the described system.

Certain embodiments comprise a system configured for delivering fluid to a negative pressure wound therapy dressing, wherein the system comprises a biasing mechanism configured to compress a fluid reservoir. In particular embodiments, the system comprises a housing configured to receive a fluid reservoir. In specific embodiments, the biasing mechanism is configured to secure a fluid reservoir within the housing. In certain embodiments, the biasing mechanism is configured as a spring. In particular embodiments the spring is a constant-force spring. In certain embodiments, the positive pressure exerted on the fluid in the reservoir is greater than or equal to approximately 75 mm Hg.

In particular embodiments, the fluid reservoir is a polyethylene bag. Specific embodiments comprise a control circuit configured to control a flow of fluid from the fluid reservoir. In certain embodiments, the control circuit is coupled to a flow sensor configured to detect the flow rate of fluid from the fluid reservoir and to provide a fluid flow rate signal to the control circuit. In particular embodiments, the control circuit is coupled to a flow controller. The flow controller may be adapted to be positioned in fluid communication between the fluid reservoir and the wound therapy dressing. In specific embodiments, the flow controller is configured as a control valve. Certain embodiments also comprise a conduit in fluid communication with a wound dressing. Particular embodiments also comprise a negative pressure source in fluid communication with the wound dressing. In specific embodiments, the biasing mechanism is disposed within a receptacle configured to extend from a housing.

Certain embodiments also include a method of delivering a fluid to a wound dressing. The method comprises exerting a force from a biasing mechanism on a fluid reservoir and compressing the fluid reservoir, wherein a fluid is directed from the fluid reservoir to the wound dressing via a conduit. Specific embodiments further comprise controlling a flow of fluid from the fluid reservoir via a flow controller. In particular embodiments, the flow controller is controlled by a control circuit. In certain embodiments, the biasing mechanism is a spring. Particular embodiments also comprise securing the fluid reservoir within a housing via the biasing mechanism. Exerting the force from the biasing mechanism may create a positive pressure on the fluid in the reservoir that is, for example, greater than or equal to approximately 75 mm Hg. Certain embodiments also comprise providing a negative pressure to the wound dressing.

Particular embodiments also include a method of providing instillation fluid and negative pressure to a wound dressing. The method comprises: applying negative pressure to the wound dressing while inhibiting instillation fluid flow to the wound dressing; ceasing to apply negative pressure to the wound dressing and measuring a volumetric leak rate from the wound dressing; enabling instillation fluid flow to the wound dressing; measuring the flow rate of the instillation fluid and the pressure at the wound dressing; verifying wound dressing pressure is approximately atmospheric pressure; ceasing the flow of instillation fluid to the wound dressing; allowing the instillation fluid to remain in the wound dressing; and removing the instillation fluid from the wound dressing.

In particular embodiments, enabling instillation fluid flow to the wound dressing comprises creating a pressure in a fluid reservoir by exerting a force from a biasing mechanism. In certain embodiments, the biasing mechanism is a spring.

Specific embodiments also include a system for treating a wound with a wound dressing. The system comprises: a housing with a receptacle configured to receive a fluid reservoir; a biasing mechanism disposed within the receptacle for compressing the fluid reservoir; a negative pressure source disposed within the housing; and a conduit for fluidly connecting the reservoir, the negative pressure source, and the wound dressing. In particular embodiments, the biasing mechanism is a spring. In certain embodiments, the negative pressure source comprises a vacuum pump and a negative pressure controller. The vacuum pump and the negative pressure controller may be adapted to be controlled by a control circuit according to a negative pressure input signal received from the wound therapy dressing. In particular embodiments, the receptacle is slideably received within the housing and configured to extend from the housing. Certain embodiments also comprise a flow sensor and a flow controller coupled to the conduit. The flow sensor and the flow controller may be adapted to be positioned in fluid communication between the fluid reservoir and the wound therapy dressing.

In yet another embodiment, provided is a system adapted to deliver fluid to a wound therapy dressing including a negative pressure source, a housing, a biasing mechanism, and a control circuit. The negative pressure source is adapted to be in fluid communication with the wound therapy dressing to provide negative pressure to the wound therapy dressing. The housing is adapted to receive a fluid reservoir, the fluid reservoir adapted to be in fluid communication with the wound therapy dressing to provide fluid from the fluid reservoir to the wound therapy dressing. The biasing mechanism is adapted to secure the fluid reservoir in the housing and to exert a positive pressure on the fluid in the fluid reservoir. The control circuit is adapted to control the negative pressure in the wound therapy dressing.

In yet another embodiment, provided is a system adapted to deliver fluid to a wound therapy dressing including a negative pressure source, a housing, a flow sensor, a flow controller, and a control circuit. The negative pressure source is adapted to be in fluid communication with the wound therapy dressing to provide negative pressure to the wound therapy dressing. The housing is adapted to receive a fluid reservoir, the fluid reservoir adapted to be in fluid communication with the wound therapy dressing to provide fluid from the fluid reservoir to the wound therapy dressing. The flow sensor is adapted to be positioned in fluid communication between the fluid reservoir and the wound therapy dressing and to detect a flow rate of the fluid from the fluid reservoir to the wound therapy dressing. The flow controller is adapted to be positioned in fluid communication between the fluid reservoir and the wound therapy dressing and to control a flow of the fluid from the fluid reservoir to the wound therapy dressing. The control circuit is adapted to control the negative pressure source. Additionally, the control circuit is adapted to receive a fluid flow rate signal from the flow sensor that corresponds to the flow rate of the fluid from the fluid reservoir and a negative pressure signal that corresponds to the negative pressure in the wound therapy dressing.

In yet another embodiment, disclosed is a method of providing instillation fluid and negative pressure to a wound dressing including: applying negative pressure to the wound dressing; ceasing to apply negative pressure to the wound dressing when the negative pressure in the wound dressing reaches a target negative pressure; measuring a volumetric leak rate of the negative pressure from the wound dressing; enabling instillation fluid flow to the wound dressing after the wound dressing reaches the target negative pressure, wherein the instillation fluid flow to the wound dressing is substantially inhibited prior to the negative pressure in the wound dressing reaching the target negative pressure and the volumetric leak rate being measured; measuring a flow rate of the instillation fluid to the wound dressing; monitoring the negative pressure in the wound dressing as the instillation fluid flows into the wound dressing; ceasing the instillation fluid flow to the wound dressing when the negative pressure in the wound dressing is approximately atmospheric pressure; allowing the instillation fluid to remain in the wound dressing for a predetermined time period; and removing the instillation fluid from the wound dressing after the predetermined time period.

In yet another embodiment, disclosed is a method of providing instillation fluid and negative pressure to a wound dressing including applying negative pressure to the wound dressing until the negative pressure in the wound dressing reaches a target negative pressure; determining a required volumetric flow rate of the negative pressure to the wound dressing to maintain the negative pressure in the wound dressing substantially at the target negative pressure, the required volumetric flow rate of the negative pressure substantially corresponding to a volumetric leak rate of the negative pressure from the wound dressing; enabling instillation fluid flow to the wound dressing after the wound dressing reaches the target negative pressure; monitoring the negative pressure in the wound dressing as the instillation fluid flows into the wound dressing; applying negative pressure to the wound dressing while the instillation fluid flows into the wound dressing, wherein a flow rate of the negative pressure applied while the instillation fluid flows substantially corresponds to the volumetric leak rate of the negative pressure from the wound dressing; and ceasing the instillation fluid flow to the wound dressing when the negative pressure in the wound dressing is approximately atmospheric pressure.

Other features and associated advantages will become apparent with reference to the following detailed description of specific embodiments in connection with the accompanying drawings.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "negative pressure" refers to an absolute pressure that is lower than the absolute atmospheric pressure at the location of use of the device. A stated level of negative pressure in a region is therefore a relative measure between the absolute atmospheric pressure and the absolute pressure in the region. A statement that the negative pressure is decreasing means the pressure in the region is moving towards atmospheric pressure (i.e. the absolute pressure is increasing). Where numeric values are used a negative sign is placed in front of the numeric pressure value to indicate the value is a negative pressure relative to atmospheric pressure.

BRIEF DESCRIPTION OF THE DRAWINGS

The following drawings form part of the present specification and are included to further demonstrate certain aspects of exemplary embodiments of the subject matter described herein.

DETAILED DESCRIPTION OF EXEMPLARY EMBODIMENTS

Various features and advantageous details are explained more fully with reference to the non-limiting embodiments that are illustrated in the accompanying drawings and detailed in the following description. For brevity, descriptions of well known starting materials, processing techniques, components, and equipment may be omitted. It should be understood, however, that the detailed description, the specific examples, and embodiments are given by way of illustration only, and not by way of limitation. Various substitutions, modifications, additions, and/or rearrangements within the scope of this specification will become apparent to those skilled in the art.

Figure 1:
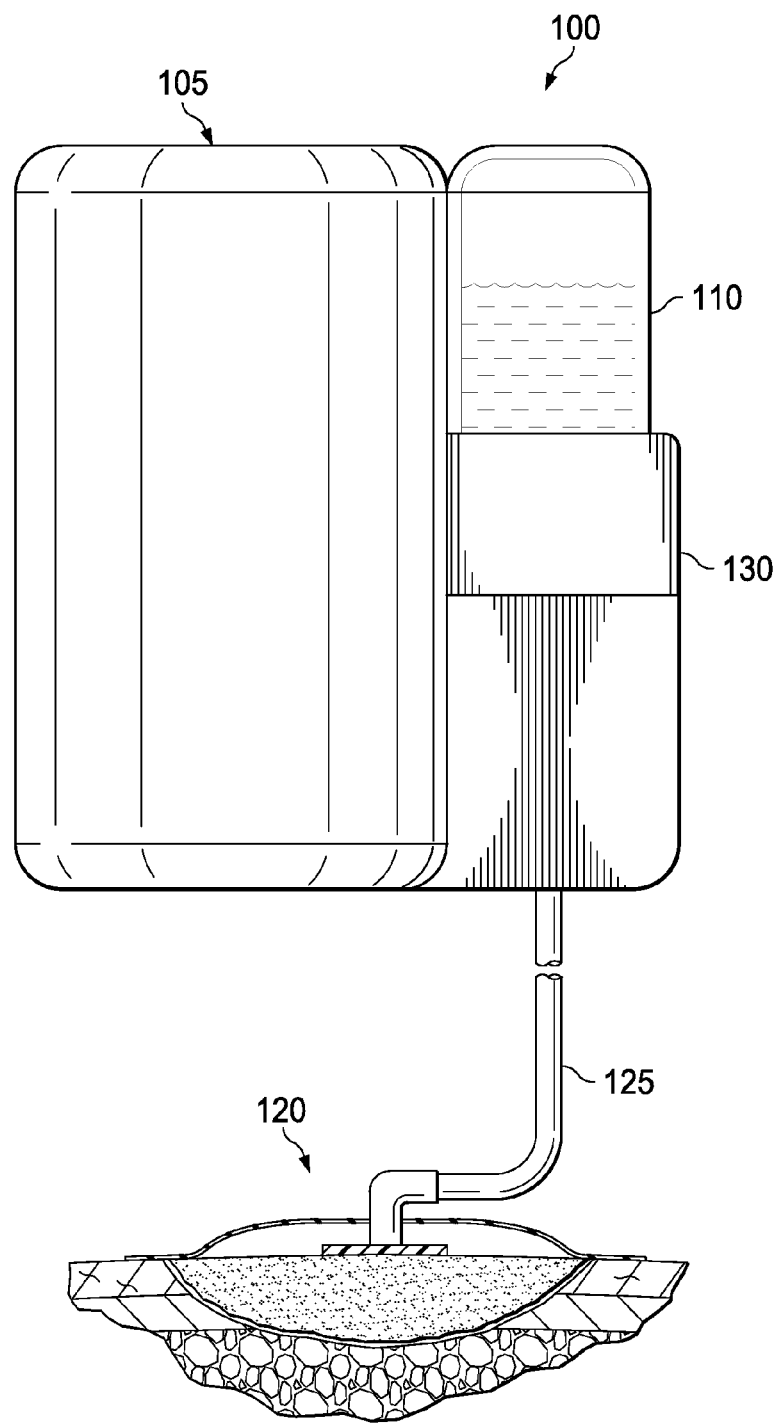
FIG. 1 is a schematic diagram illustrating one embodiment of a system for delivering fluid to a wound therapy dressing.
Figure 2:
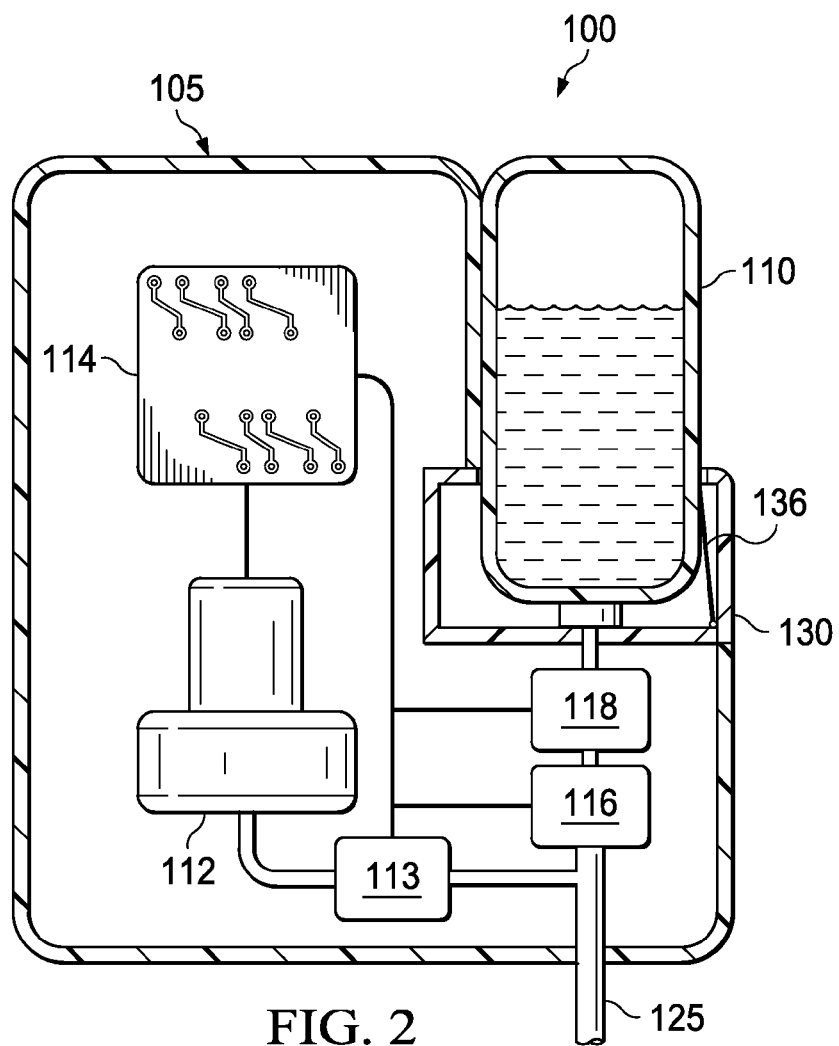
FIG. 2 is a section view of the embodiment of FIG. 1.
Figure 3:
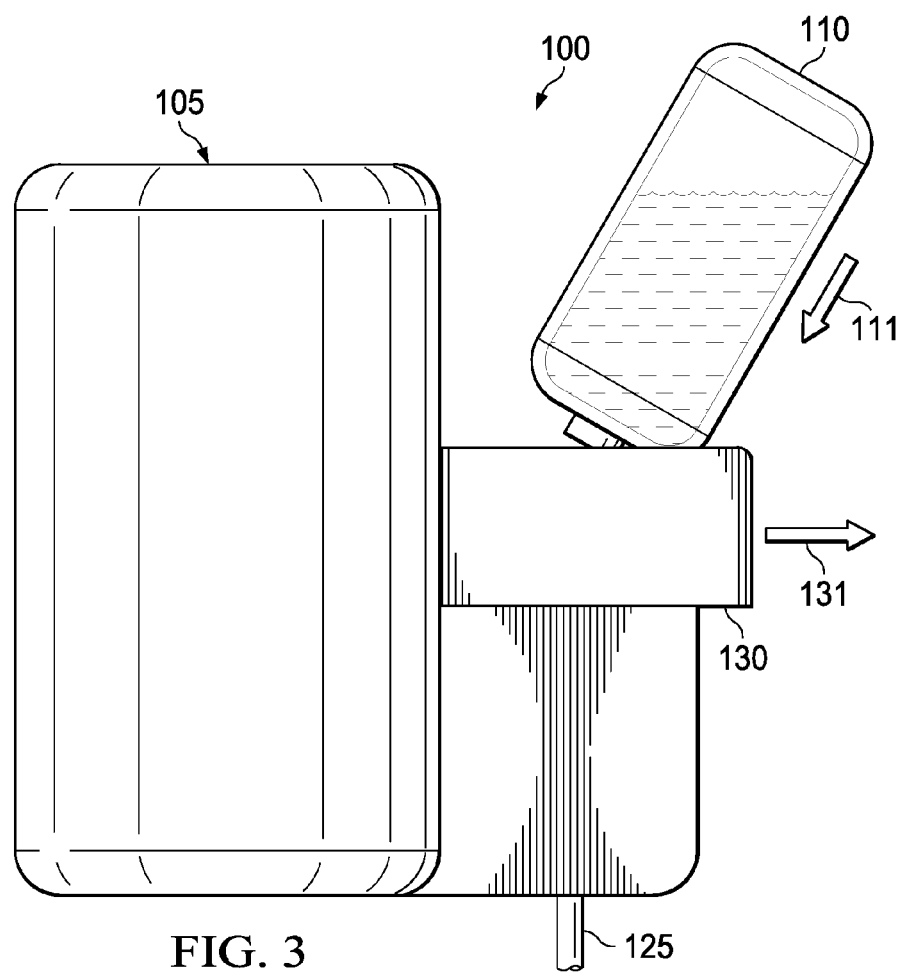
FIG. 3 is a schematic diagram illustrating the embodiment of FIG. 1 during insertion of a fluid reservoir.

FIGS. 1-3 illustrate an exemplary embodiment of a system 100 for providing fluid delivery to a wound therapy dressing. As shown, system 100 includes a housing 105 with a receptacle 130 configured to receive a reservoir 110. In this embodiment, system 100 further comprises a conduit 125 and a wound dressing 120. Conduit 125 may be, for example, a muli-lumen conduit including more than one individual lumen or tube (not shown) housed within conduit 125. The individual lumens or tubes within conduit 125 may be in fluid communication with wound dressing 120. Each lumen or tube may be utilized for a different purpose, such as, for example, instillation of fluid to wound dressing 120, communication of negative pressure to wound dressing 120, and receipt of negative pressure feedback from wound dressing 120 as described further below. Reservoir 110 may be, for example, configured as a polyethylene bag similar to those used for intravenous fluid delivery. Compression of reservoir 110 can exert a positive pressure on fluid in reservoir 110 and force the fluid from reservoir 110 as described in more detail below.

As shown in FIG. 2, receptacle 130 comprises a biasing mechanism 136 configured to securely position reservoir 110. In addition, biasing mechanism 136 is configured to compress reservoir 110 by exerting an external force on reservoir 110. Continuing with FIG. 2, housing 105 of system 100 may include a negative pressure source 112, a negative pressure controller 113, a control circuit 114, a flow controller 116 and a flow sensor 118. Negative pressure source 112 may be, for example, a vacuum pump. Negative pressure controller 113 may be a valve, including for example, a control valve or a manually operated valve. Flow controller 116 may also be configured as a valve, including a control valve in certain embodiments.

Referring now to FIG. 3, housing 105 may be configured to receive reservoir 110. As shown in FIG. 3, receptacle 130 may be moved away from housing 105 in the direction indicated by arrow 131 for insertion of reservoir 110 into receptacle 130 in the direction indicated by arrow 111. Receptacle 130 can then be moved toward housing 105 (e.g., in the direction opposite of arrow 131) so that reservoir 110 is received by housing 105 and in fluid communication with conduit 125, as depicted in FIGS. 1-2. The exemplary embodiment of FIG. 3 depicts receptacle 130 slidably received within housing 105 and configured to extend from housing 105 in a lateral direction for insertion of reservoir 110 into receptacle 130. In another embodiment, receptacle 130 may be configured to extend from housing 105 in any suitable direction for inserting reservoir 110. In yet another embodiment, receptacle 130 may be coupled to housing 105 and stationary relative to housing 105.

With reservoir 110 in the position shown in FIGS. 1 and 2, system 100 is ready for operation. Biasing mechanism 136 is configured to bias reservoir 110 toward housing 105, thereby securing reservoir 110. Extending receptacle 130 from housing 105 as described above reduces the bias from biasing mechanism 136 on reservoir 110 so that a user may more easily insert reservoir 110 into receptacle 130. In addition, biasing mechanism 136 is configured to compress reservoir 110, thereby exerting a positive pressure on fluid in reservoir 110. The compression of reservoir 110 from biasing mechanism 136 exerts a positive pressure on the fluid, in reservoir 110, providing fluid flow from reservoir 110 through conduit 125 without the need for an external pumping mechanism (e.g, a peristaltic pump). The ability to provide fluid flow from reservoir 110 to wound dressing 120 without a separate pumping mechanism can greatly reduce the complexity of a wound therapy system that provides both negative pressure treatment and fluid instillation. Such a configuration can also reduce the power requirements associated with fluid delivery.

Biasing mechanism 136 may be configured as a constant-force type spring adapted to deliver a substantially constant mechanical load over a full length of travel of the spring. The pressure created by biasing mechanism 136 in reservoir 110 may reduce the potential for inconsistencies in fluid flow experienced by system 100 caused by, for example, height differences between wound dressing 120 and reservoir 110. In an exemplary embodiment, biasing mechanism 136 may exert a substantially constant pressure on reservoir 110 that is greater than the pressure required to hold a static column of instillation fluid to a height approximating the typical distance reservoir 110 may be positioned below wound dressing 120 during use For example, biasing mechanism 136 may exert a substantially constant pressure on reservoir 110 of approximately 75 mm Hg, corresponding to the pressure required to hold a static column of instillation fluid to a 1 meter height. In other exemplary embodiments, biasing mechanism 136 may be configured to exert pressure greater than or less than 75 mm Hg.

Referring to FIG. 2, in operation, fluid in conduit 125 is directed through flow sensor 118 and flow controller 116. Flow sensor 118 and flow controller 116 are electrically coupled to control circuit 114 and in fluid communication with conduit 125 between fluid reservoir 110 and wound dressing 120. Flow sensor 118 can detect the rate and/or volume of fluid flow from reservoir 110 through conduit 125 and provide a corresponding measurement signal, such as a fluid flow rate signal, to control circuit 114. Based on the measurement signal from flow sensor 118, control circuit 114 can send a control signal to flow controller 116 to control the flow of fluid through conduit 125 to wound dressing 120. For example, if the flow rate is detected to be greater than desired, control circuit 114 can send a signal to flow controller 116 to reduce the amount of fluid flow to wound dressing 120. In one embodiment, flow controller 116 may be a control valve adapted to reduce the amount of fluid flow by partial or complete closure of the control valve. In another embodiment, flow controller 116 may stop fluid flow to wound dressing 120 after a particular volume of fluid has been delivered to wound dressing 120. The volume of fluid may be calculated, for example, based on the fluid flow rate and the length of time of fluid flow.

Figure 4:
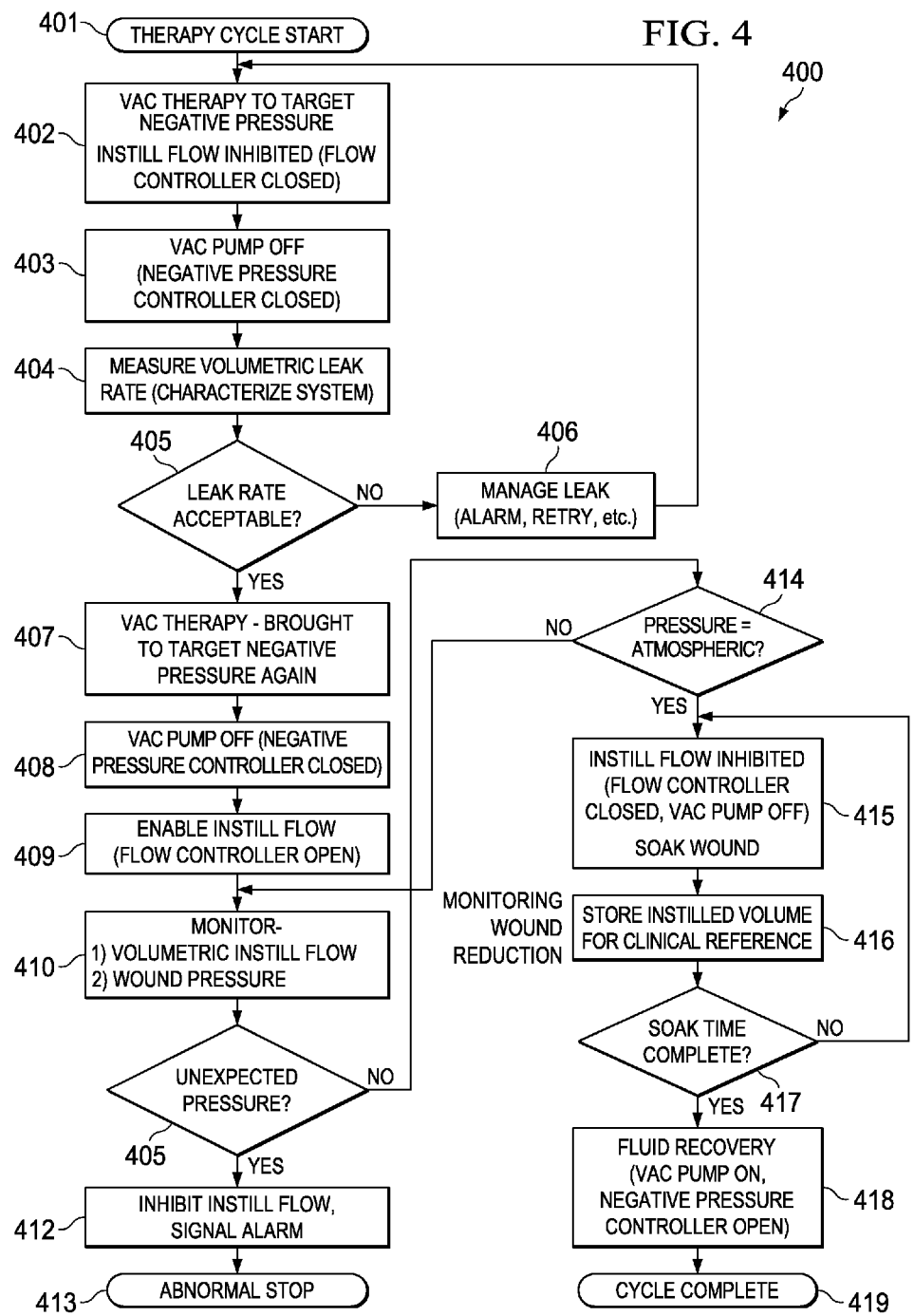
FIG. 4 is schematic flowchart diagram illustrating one embodiment of a method for delivering fluid to a wound therapy dressing.

Referring now to FIG. 4, a flow chart is provided to illustrate an exemplary method for operating system 100. The order and labeled steps of the method depicted in FIG. 4 are indicative of one non-limiting embodiment. The format and symbols employed are understood not to limit the scope of the method, or the order of execution of the steps depicted in the method.

As illustrated in FIG. 4, a method 400 depicted therein includes steps that may be executed for the operation of an exemplary system according to this disclosure, including system 100 of FIGS. 1-3. Certain embodiments may include a tangible computer readable medium comprising computer readable code that, when executed by a computer, causes the computer to perform operations and calculations comprising the steps described herein and depicted in FIG. 4.

Continuing with FIG. 4, step 401 represents the start of the therapy cycle. Step 402 includes bringing system 100 to a target negative pressure (via negative pressure source 112 and negative pressure controller 113) while inhibiting the instillation fluid flow (e.g., by maintaining flow controller 116 in the closed position). Step 403 includes turning off negative pressure source 112 and/or closing negative pressure controller 113 in system 100 when the target negative pressure has been attained in wound dressing 120.

Control circuit 114 may be adapted to control negative pressure source 112 for bringing wound dressing 120 up to the target negative pressure, or otherwise regulating the negative pressure in wound dressing 120. For example, control circuit 114 may be adapted to receive a negative pressure signal that corresponds to the negative pressure in wound therapy dressing 120. Control circuit 114 may control the application of negative pressure from negative pressure source 112 to wound therapy dressing 120 by, for example, sending a signal to negative pressure controller 113 and/or negative pressure source 112 to increase or decrease the negative pressure applied to wound dressing 120 according to the negative pressure signal. Control circuit 114 may receive the negative pressure signal from, for example, a negative pressure feedback lumen (not shown) in fluid communication with a pressure sensor (not shown) associated with control circuit 114. The negative pressure feedback lumen may be housed within conduit 125, providing a multi-lumen configuration for conduit 125. In other embodiments, the negative pressure feedback lumen may be coupled to wound dressing 120 separate from conduit 125.

The volumetric leak rate of system 100 and wound dressing 120 can be characterized in step 404, followed by an evaluation of whether the volumetric leak rate is acceptable in step 405. If the volumetric leak rate is not acceptable, the user can address the cause of the leak rate in step 406 and return to step 402 in the method.

The volumetric leak rate of the negative pressure from wound dressing 120 may be substantially equal to a volumetric flow rate of the negative pressure to wound dressing 120 that is required to maintain the negative pressure in wound dressing 120 substantially at the target negative pressure. Thus, the volumetric leak rate may be measured, or characterized, by determining a required volumetric flow rate of the negative pressure to wound dressing 120 for maintaining the negative pressure in wound dressing 120 substantially at the target negative pressure. The required volumetric flow rate of the negative pressure may be determined, for example, by successively decreasing the volumetric flow rate of the negative pressure to wound dressing 120 as wound dressing 120 approaches the target negative pressure. The required volumetric flow rate of the negative pressure to wound dressing 120 is measured when the volumetric flow rate is decreased to a value that maintains wound dressing 120 at the target negative pressure without fluctuation of the negative pressure, i.e., a steady state condition. A processor including software that is associated with control circuit 114 may be employed to monitor the negative pressure in wound dressing 120 and the volumetric flow rate of the negative pressure from negative pressure source 112 as wound dressing 120 reaches the steady state condition at the target negative pressure.

Once the volumetric leak rate has been determined to be acceptable, a user can again bring the system to the target negative pressure in step 407 as previously described for step 402. Negative pressure source 112 can then be turned off and/or negative pressure controller 113 closed in step 408, followed by enabling instillation fluid flow in step 409, e.g, by opening a valve in system 100, such as flow controller 116. Biasing mechanism 136 can provide sufficient positive pressure on fluid in fluid reservoir 110 to enable instillation fluid flow in step 409 without the use of a separate pumping mechanism as previously described. In addition, instillation fluid flow may be enabled by operation of the negative pressure in wound dressing 120 drawing fluid from fluid reservoir 110 into wound dressing 120. As fluid from reservoir 110 enters wound dressing 120, the negative pressure in wound dressing 120 gradually approaches or otherwise returns to atmospheric pressure, i.e., the negative pressure decreases. In one embodiment, biasing mechanism 136 may be omitted.

In step 410, system 100 can monitor the volumetric flow rate of the instillation fluid, as well as the negative pressure at wound dressing 120. The monitored parameters of system 100 can be evaluated in step 411 to determine, for example, whether an unexpected change in pressure is present, such as the negative pressure at wound dressing 120 returning to atmospheric pressure sooner than expected based on the previously-measured volumetric leak rate. If the pressure change is not acceptable, the instillation fluid flow can be discontinued in step 412 and operation of system 100 can be terminated in step 413.

If the pressure is changing at an acceptable rate (e.g., due to the flow of instillation fluid from reservoir 110 to wound dressing 120), system 100 can verify that the pressure has reached atmospheric pressure in step 414. System 100 may then stop the flow of instillation fluid in step 415 (e.g., by closing flow controller 116 in the instillation fluid flow path) and allow the wound to soak for a predetermined time period. The predetermined time period may be any suitable time period determined by a clinician as appropriate for the circumstances. In step 416, system 100 can store the instilled volume for clinical reference and monitor the wound reduction. The wound reduction, or healing of the wound, may reduce the total volume of fluid instilled into wound dressing 120 by the method described above.

In one embodiment (not shown), the method may include the step of applying negative pressure to wound dressing 120 while the fluid from reservoir 110 flows into wound dressing 120. The flow rate of the negative pressure applied while the fluid flows into wound dressing 120 may substantially correspond to the previously-measured volumetric leak rate of the negative pressure from wound dressing 120. In this manner, system 100 can enhance the accuracy of the volume of the fluid from reservoir 110 drawn into wound dressing 120 by operation of the negative pressure in wound dressing 120, i.e., the decreasing negative pressure in wound dressing 120 corresponds substantially to the fluid from reservoir 120 being instilled into wound dressing 120 rather than leakage of the negative pressure from wound dressing 120.

System 100 can then determine if the soak time is complete in step 417. If the soak time is not complete, system 100 can continue to soak the wound as described in step 415. If the soak time is determined to be complete, system 100 can recover fluid in step 418 (e.g. by operating the negative pressure source 112 and opening negative pressure controller 113 to apply negative pressure to wound dressing 120). The cycle can then be completed in step 419 and system 100 can be powered off.

In one embodiment (not shown), the method may include determining a total volume of the fluid flow from reservoir 110 into wound dressing 120. The total volume of the fluid flow may substantially correspond to the flow rate of the fluid into wound dressing 120 and a time period required for wound dressing 120 to reach approximately atmospheric pressure after enabling the fluid flow to wound dressing 120. As the method described above is utilized during various stages of healing of a particular wound, variations in the total volume of fluid instilled into wound dressing 120 may be logged and compared to one another to indicate a rate of healing or reduction for the particular wound.

While the apparatus and methods herein have been described in terms of preferred embodiments, it will be apparent to those of skill in the art that variations may be applied without departing from the scope of this specification as defined by the appended claims.

We claim:

1. A system adapted to deliver fluid to a wound therapy dressing, comprising:
    a negative pressure source adapted to be in fluid communication with the wound therapy dressing to provide negative pressure to the wound therapy dressing;
    a housing adapted to receive a fluid reservoir, the fluid reservoir adapted to be in fluid communication with the wound therapy dressing to provide fluid from the fluid reservoir to the wound therapy dressing;
    a biasing mechanism adapted to secure the fluid reservoir in the housing and to exert a positive pressure on the fluid in the fluid reservoir; and
    a control circuit adapted to control the negative pressure in the wound therapy dressing;
    wherein the biasing mechanism is a spring adapted to be in direct engagement with the fluid reservoir.

2. The system of claim 1, wherein the negative pressure source is disposed within the housing.

3. The system of claim 1, wherein the biasing mechanism is configured to compress the fluid reservoir to secure the fluid reservoir within the housing and to exert the positive pressure on the fluid in the fluid reservoir.

4. The system of claim 1, wherein the spring is a constant-force spring.

5. The system of claim 1, wherein the positive pressure exerted on the fluid in the fluid reservoir is at least approximately 75 mm Hg.

6. The system of claim 1, wherein the fluid reservoir is a polyethylene bag.

7. The system of claim 1, wherein the control circuit is configured to control a flow of the fluid from the fluid reservoir to the wound therapy dressing and to detect a flow rate of the fluid from the fluid reservoir to the wound therapy dressing.

8. The system of claim 7, wherein the control circuit is coupled to a flow sensor configured to detect the flow rate of the fluid from the fluid reservoir and to provide a fluid flow rate signal to the control circuit.

9. The system of claim 1, wherein the control circuit is coupled to a flow controller adapted to be positioned in fluid communication between the fluid reservoir and the wound therapy dressing.

10. The system of claim 9, wherein the flow controller is a control valve.

11. The system of claim 8, wherein the flow sensor is adapted to be positioned in fluid communication between the fluid reservoir and the wound therapy dressing.

12. The system of claim 1, wherein the negative pressure source comprises a vacuum pump and a negative pressure controller, wherein the control circuit is adapted to control the vacuum pump and the negative pressure controller according to a negative pressure signal received from the wound therapy dressing.

13. The system of claim 1, wherein the biasing mechanism is disposed within a receptacle, the receptacle slidably received within the housing and configured to extend from the housing.

14. A system adapted to deliver fluid to a wound therapy dressing, comprising:
    a negative pressure source adapted to be in fluid communication with the wound therapy dressing to provide negative pressure to the wound therapy dressing;
    a housing adapted to receive a fluid reservoir, the fluid reservoir adapted to be in fluid communication with the wound therapy dressing to provide fluid from the fluid reservoir to the wound therapy dressing;
    a biasing mechanism adapted to exert a positive pressure on the fluid in the fluid reservoir;
    a flow sensor adapted to be positioned in fluid communication between the fluid reservoir and the wound therapy dressing and to detect a flow rate of the fluid from the fluid reservoir to the wound therapy dressing;
    a flow controller adapted to be positioned in fluid communication between the fluid reservoir and the wound therapy dressing and to control a flow of the fluid from the fluid reservoir to the wound therapy dressing; and
    a control circuit adapted to control the negative pressure source and the flow controller, the control circuit further adapted to receive a fluid flow rate signal from the flow sensor that corresponds to the flow rate of the fluid from the fluid reservoir and a negative pressure signal that corresponds to the negative pressure in the wound therapy dressing;

wherein the biasing mechanism is a spring adapted to be in direct engagement with the fluid reservoir.

15. The system of claim 14, wherein the fluid reservoir is a polyethylene bag.

16. The system of claim 14, wherein the flow controller is a control valve adapted to be controlled by the control circuit.

17. The system of claim 14, wherein the biasing mechanism is a constant-force spring.

18. The system of claim 17, wherein the biasing mechanism is disposed within a receptacle to secure the fluid reservoir in the housing, the receptacle slidably received within the housing and configured to extend from the housing.

19. The system of claim 17, wherein the positive pressure on the fluid in the fluid reservoir is at least approximately 75 mm Hg.

20. The system of claim 14, wherein the negative pressure source comprises a vacuum pump and a negative pressure controller, the control circuit adapted to control the vacuum pump and the negative pressure controller according to the negative pressure signal.

* * * * *